United States Patent
Barsch

(10) Patent No.: US 6,234,177 B1
(45) Date of Patent: May 22, 2001

(54) APPARATUS AND METHOD FOR DEPLOYING AN EXPANDABLE BIOPSY MARKER

(75) Inventor: Thomas Barsch, 3777 S. Albion, Englewood, CO (US) 80110

(73) Assignee: Thomas Barsch, Englewood, CO (US)

( * ) Notice: Subject to any disclaimer, the term of this patent is extended or adjusted under 35 U.S.C. 154(b) by 0 days.

(21) Appl. No.: 09/373,351

(22) Filed: Aug. 12, 1999

(51) Int. Cl.⁷ ..................................................... A61B 19/00
(52) U.S. Cl. ......................... 128/897; 600/424; 600/431; 606/116
(58) Field of Search ..................................... 128/897–898; 606/116; 600/424, 427, 431, 562, 567, 566

(56) References Cited

U.S. PATENT DOCUMENTS

| | | |
|---|---|---|
| 4,007,732 | 2/1977 | Kvavle et al. . |
| 4,790,329 | 12/1988 | Simon . |
| 5,108,407 | 4/1992 | Geremia et al. . |
| 5,195,540 | 3/1993 | Shiber . |
| 5,213,100 | 5/1993 | Summ . |
| 5,409,004 | 4/1995 | Sloan . |
| 5,456,713 | 10/1995 | Chuter . |
| 5,487,392 | 1/1996 | Haaga . |
| 5,782,764 | 7/1998 | Werne . |
| 5,853,366 * | 12/1998 | Dowlatshahi ........................ 606/116 |
| 5,879,357 | 3/1999 | Heaton et al. . |

OTHER PUBLICATIONS

Brochure: Deployment of the MicroMark™ Tissue Marker (C1535 with the MAMMOTOME® II Gauge Probe.
Brochure: Biopsys Mammotome® Biopsy System.

* cited by examiner

Primary Examiner—John P. Lacyk
(74) Attorney, Agent, or Firm—Swanson & Bratschun, LLC

(57) ABSTRACT

An apparatus for marking the location of a void of body tissue created by a biopsy consists of a deployment catheter having an axial catheter lumen and distal opening. A resilient imaging marker which is self-biased into an expanded state and compactable into a compacted state is axially received in its compacted state in the catheter lumen. The plunger is axially received in the lumen of the deployment catheter and is axially advancable between a deploying position and a deployed position. The plunger has a leading end configured to drive the imaging marker out the distal opening of the deployment catheter upon axial advancement of the plunger form the deploying position to the deployed position. A method for marking a location of a void of body tissue created by a biopsy includes providing a deployment catheter having an axial lumen and a distal opening with an imaging marker in the axial lumen. The distal opening of the catheter is advanced to the void of body tissue. The imaging marker is axially advanced to the distal opening and expanded as it reaches the opening to extend into the void of body tissue. Thereafter the imaging marker is displaced from the opening.

22 Claims, 8 Drawing Sheets

APPARATUS AND METHOD FOR DEPLOYING AN EXPANDABLE BIOPSY MARKER

TECHNICAL FIELD

The present invention is directed toward biopsy markers, and more particularly toward an apparatus and method for deploying an expandable imaging biopsy marker.

BACKGROUND ART

In recent years, advancements in the design and surgical biopsy needles and their use have enabled practitioners to extract substantial volumes of tissue using surgical biopsy needles as opposed to more invasive surgical procedures.

One representative biopsy needle system is the MAMATOME® Breast Biopsy System of Biopsis Medical, Inc., Irvine, Calif. The MAMATOME® Breast Biopsy System uses a dual-lumen biopsy needle 10 shown in cross-section in FIG. 1. The biopsy needle 10 has a sidewall 12 and an inner wall 14. The inner wall 14 divides the interior of the biopsy needle into a main lumen 16 and a vacuum lumen 18. The distal end 20 of the dual-lumen biopsy needle is pointed to facilitate ease of insertion into the tissue of a patient. Proximate the distal end 20 of the dual-lumen biopsy needle an aperture 16 extends through the sidewall 12 and communicates with the main lumen 16. The inner wall 14 has a plurality of holes 24 corresponding to the aperture 22.

In use, under stereotactic or ultrasonic guidance, the needle is positioned within the affected tissue 25 to align the aperture 22 with the suspect lesion. A vacuum is then applied to the vacuum lumen 18 to aspirate tissue into the aperture 22. Thereafter a rotating cutter 26 is axially advanced within the main lumen 16 cutting and capturing a specimen in the cavity 28. The vacuum is then stopped, the rotating cutter 26 is axially withdrawn from the main lumen 16 and thereafter the tissue specimen can be removed from the cavity 28. A void 30 remains in affected tissue. The dual-lumen biopsy needle 10 can be axially rotated about axis A so that more tissue can be drawn into the aperture 22, severed and removed using the rotating cutter as discussed above. If the doctor should elect to rotate the biopsy needle about axis A 360 degrees so as to remove a maximum amount of tissue, a considerable void can be left in the affected tissue of the patient.

Typically, the biopsy is being performed to determine whether the lesion is cancerous. If so, subsequent surgery may be required to remove further tissue from around the now created void. In order to mark the site of the biopsy, the prior art has developed a number of marking apparatus. One representative marking apparatus is the MICROMARK™ II Tissue Marker of Biopsis Medical, Inc. This device has a flexible introducer with a radiographic tissue marker or clip at its distal end. The flexible introducer is axially inserted in the main lumen 16 of the biopsy needle. When the distal end of the flexible introducer reaches the aperture 16, it is biased to extend out of the aperture. Thereafter, a release button on a deployment actuator is pushed which causes axial advancement and disengagement of the clip, which is substantially configured as a staple, into the wall of the void 30. Thereafter, the flexible introducer and the biopsy needle can be removed from the affected tissue with the marker indicating the approximate biopsy site.

One problem with the MICROMARK™ II Tissue Marker is that it requires a complicated deployment structure that is subject to failure. It is a reoccurring problem that the clip does not actually disengage when the deployment catheter is pushed. A more pronounced problem with this type of marking system is evident when the biopsy is conducted on breast tissue. Referring to FIGS. 2A and 2B, typically when a mammogram is performed, the breast 32 is compressed between a pair of plates 34, 36 and the biopsy is performed with the breast in compression. When the clip, 32 is inserted using the MICROMARK™ II Tissue Marker or similar devices, the position of the clip is satisfactory with the breast in compression. However, since the clip is embedded into the tissue adjacent to the cavity, when compression is removed and the breast is returned to its natural state, the clip will migrate relative to the biopsy void 30 as illustrated in FIGS. 3A and 3B. This has the unfortunate result of not leaving the clip in the precise location of the biopsy void. Thus, if analysis of the removed tissue indicates a need for further surgery to remove more tissue around the site of the biopsy, the surgeon may be directed to the wrong site when the clip is later located using imaging techniques. This can result in the surgeon having to remove more tissue than may have been required had the site of the biopsy void been accurately marked, possibly resulting in undue physical deformity and increased surgical morbidity. In a worst case, the surgeon may even miss removing cancerous tissue because of the mis-marking of the site of the biopsy, leaving the patient subject to the risk of a malignant tumor.

In addition to the MICROMARK™ II Tissue Marker described above, there are other prior art systems intended to mark the site of a biopsy. These systems are designed for surgical removal shortly after deployment. They have in common a wire or cable extensions to the skin or surface of an organ. For example, Heaton, U.S. Pat. No. 5,879,357, teaches a marker having slats including a living hinge. The slats are laterally expandable to mark a suspect lesion. However, the doctor must actuate the slats into their expanded position which complicates the process of marking the biopsy void. In addition, Heaton requires a cable which is "sufficiently rigid" to assist in maintaining the marker in a deployed position. This cable remains attached to the implanted marker. This structure has the obvious disadvantage that the cable provides a vehicle for infection. Moreover, in the event the analysis of the tissue is negative, presumably the marker and the cable would have to be removed from the breast, therefore subjecting the patient to further unnecessary trauma.

Simon, U.S. Pat. No. 4,790,329, teaches a springing barb as part of a needle intended to be implanted under radiological examination in a patient to mark the cite of a lesion. According to Simon, this springing barb, as well as a cannula for implanting the barb, is intended to be left in place in the breast for locating the site of a lesion for a future biopsy. Thus, the structure of Simon is not suitable for marking the site where a biopsy has been taken because, as with Heaton, if in fact no further removal of tissue is necessary because the analysis of lesion comes back negative, the structure of Simon would have to be removed somehow.

Kvavle, U.S. Pat. No. 4,007,732, teaches radiographic resilient barbs that may be compressed and loaded into an implanting device. The barbs expand upon being advanced through the inserting device. Kvavle does not teach an apparatus for marking the site of a already conducted biopsy, but rather a system for marking the site of a lesion for a future biopsy. Kvavle teaches a wire 4 connected to the barbs which extend through the skin to provide an apparatus for locating the site of future biopsy. Again, the structure of Kvavle has the same shortcomings of Simon and Heaton, namely it is not suitable for marking the site where a biopsy has already been conducted because it leaves a wire extending through the skin of the patient.

The present invention is directed toward overcoming one or more of the problems discussed above.

SUMMARY OF THE INVENTION

An apparatus for marking the location of a void of body tissue created by a biopsy consists of a needle having an axial lumen defined by a sidewall of the lumen, a proximal opening and an aperture in the sidewall extending into the lumen near the distal end of the needle. A resilient imaging marker which is self-biased into an expanded state and compactable into a compacted state, resides in its compacted state in the lumen. A plunger having a leading end and a trailing end resides in the needle. The plunger is axially advancable within the lumen between a deploying position and a deployed position with the leading end positioning the marker at the aperture in the deployed position, whereat the marker self-biases to an expanded state extending out of the aperture. Preferably, the leading end of the plunger is configured to drive the marker out of the aperture. The leading end of the plunger may be an inclined surface which, when aligned with the aperture, drives the marker out of the aperture as the plunger is axially advanced to the deployed position. The leading end of the plunger opposite the axially inclined surface is preferably a cylindrical surface with an outer diameter substantially corresponding to an inner diameter of the lumen. The cylindrical portion of the leading end, when aligned with the aperture, substantially closes the aperture. The marker is driven from the aperture by aligning the inclined surface with the aperture, axially advancing the plunger between the deploying and the deployed positions and then axially rotating the plunger to align the cylindrical portion of the leading end with the aperture. Preferably, indicia is associated with the trailing end of the catheter for indicating which of the inclined surface and the cylindrical portion of the leading end is aligned with the aperture. The resilient imaging marker is preferably made of stainless steel or memory metal. It is further preferably dimensioned so that, in its expanded state, it substantially bridges the void of body tissue.

Another aspect of the present invention is an apparatus for marking the location of a void of body tissue created by a biopsy. The apparatus consists of a deployment catheter having an axial lumen and an open distal end. A resilient imaging marker which is self-biased to an expanded state and compactable to a compacted state resides in the catheter lumen in its compacted state. A plunger is axially received in the lumen of the deployment catheter and is axially advancable within the catheter lumen between a deploying position and a deployed position. The plunger has a leading end to drive the imaging marker out of the distal end of the deployment catheter upon advancement of the plunger from the deploying position to the deployed position. The imaging marker is located between the leading end of the plunger and the open distal end of the deployment catheter with the plunger in the deploying position. The apparatus may further include a needle having an axial needle lumen and proximal and distal ends. The needle further includes proximal and distal openings extending into the needle lumen. The distal end of the deployment catheter is axially received it the proximal opening of the needle. The distal opening of the needle may be an aperture in the sidewall of the needle proximate the distal end of the needle and the leading end of the plunger may include an axially inclined surface which drives the marker out of the aperture as the leading end of the plunger is axially advanced to the deployed position with the inclined surface aligned with the aperture. The leading end of the plunger opposite the axially inclined surface is preferably cylindrical with an outer diameter substantially corresponding to an inner diameter of the catheter lumen. When the cylindrical portion of the leading end is aligned with the aperture with the plunger in the deployed position, it substantially closes the aperture. The imaging marker is driven out of the aperture by axially advancing the plunger to the deployed position with the inclined surface aligned with the aperture and then axially rotating the plunger to align the cylindrical portion of the leading end of the plunger with the aperture.

Yet another aspect of the present invention is method of marking a void of body tissue created by a biopsy. A deployment catheter having an axial lumen and a distal opening with an imaging marker in the axial lumen is provided. The distal opening of the catheter is advanced to the void of body tissue. The imaging marker is axially advanced to the distal opening and expanded as the imaging marker reaches the opening to extend into the void of body tissue. The imaging marker is then displaced from the opening.

Yet another aspect of the present invention is method of marking a void of body tissue created by a biopsy performed using a biopsy needle having an axial lumen defined by a sidewall of the needle, a proximal opening and an aperture in the sidewall extending into the lumen near a distal end of the needle, the aperture being aligned with the void of body tissue. A deployment catheter is provided having an axial lumen and an open distal end, with an expandable imaging marker in the axial lumen. The open distal end of the deployment catheter is axially inserted into the proximal opening of the needle. The imaging maker is advanced to the aperture. As the imaging marker reaches the aperture it is expanded into the void of body tissue. The maker is then displaced from the aperture. The aperture is then preferably closed. The imaging marker may be expanded to substantially bridge the void of body tissue. The expansion of the marker may be preformed by self-biasing the imaging marker in to an expanded state. Preferably, the leading end of the plunger is configured to displace the imaging marker from the aperture by axially rotating the plunger from a first to a second orientation. The leading end of the plunger may have an axially inclined surface and an opposite cylindrical surface. The axially inclined surface, when aligned with the aperture, urges the marker from the aperture as the plunger is axially advanced from a deploying position with the imaging marker in the lumen to a deployed position with the imaging marker at the aperture. The marker is displaced from the aperture by axially advancing the inclined surface in alignment with the aperture and then axially rotating the plunger to bring the cylindrical surface into alignment with the aperture.

The apparatus and method for marking the location of a biopsy of the present invention provides a marker which occupies the actual void created by the biopsy to accurately locate the site where the biopsy was performed. This facilitates removal of a minimum of tissue if subsequent surgery is required, minimizing physical deformity and patient trauma. Because the marker is not embedded into tissue adjoining the void, the marker does not migrate relative to the void under those circumstances where the subject tissue has been compressed. Moreover, the method provides for failsafe deployment of the marker in the precise location of the void while simplifying the deployment procedure, thereby minimizing present and future patient trauma. The apparatus is readily adaptable to current procedures using surgical biopsy needles or aspirating needles and represents a vast improvement over prior art marking techniques.

DETAILED DESCRIPTION OF THE PREFERRED EMBODIMENT

Figure 4A:
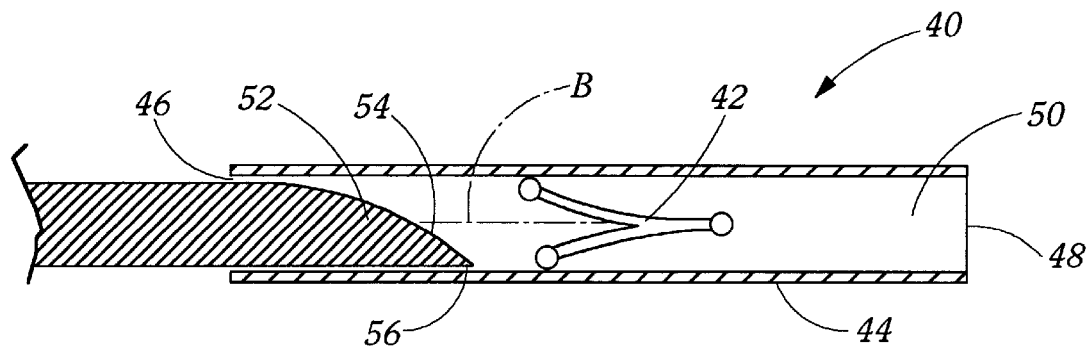
FIG. 4A is an axial cross-section of the expandable marker, deploying catheter and plunger.

An apparatus for deploying an expandable biopsy marker 40 is shown in FIG. 4A. The apparatus 40 consists of a resilient imaging marker 42 residing in a deploying catheter 44. The deploying catheter 44 has a proximal opening 46 and a distal opening 48 with a catheter lumen 50 extending therebetween. A plunger 52 is axially received in the catheter lumen 44. The plunger 52 can be a rigid rod or flexible about an axis B, provided the catheter is axially incompressible when deployed within the catheter lumen 50 and is rotatable about the axis B with minimal torsional deflection. The leading end of the plunger 52 has an axially inclined surface 54 and an opposite cylindrical surface 56. The radius of the cylindrical surface 56 substantially corresponds to the radius of the inner diameter of the deployment catheter 44.

The resilient marker 42 can take one of many configurations, some of which are illustrated herein. The important features of the imaging marker 42 are that it be made of a material that is capable of being viewed by x-ray, ultrasound, MRI or other imaging apparatus and that it be resilient or self-biased from a compacted state to an expanded state. The resilient imaging marker 42 is shown in its fully expanded state in FIGS. 7 and 8. The resilient imaging marker 42 is compactable into its compacted state so that it can be axially inserted into the catheter lumen 50. Further, the resilient imaging marker 42 must be capable of being axially advanced within the lumen 50 without snagging or jamming therein. Representative dimensions for a resilient imaging marker 42 are provided in FIG. 8.

Figure 9A:
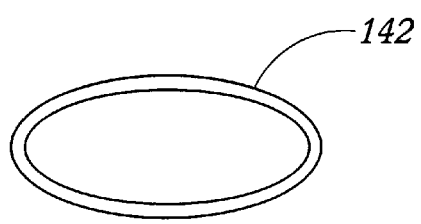
FIG. 9A is an alternate embodiment of an expandable marker in accordance with the present invention in its compacted state.
Figure 9B:
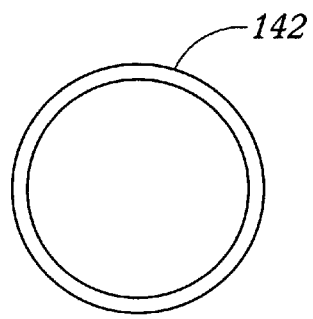
FIG. 9B shows the marker of FIG. 9A in its expanded state.
Figure 10A:
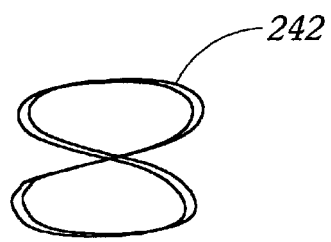
FIG. 10A is a second alternate embodiment of an expandable marker in accordance with the present invention in its compacted state.
Figure 10B:
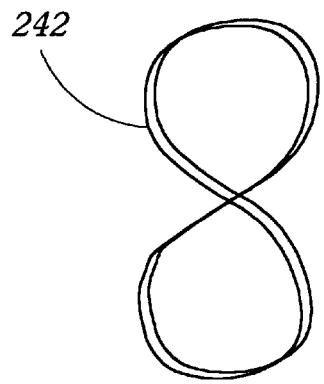
FIG. 10B is shows the marker of FIG. 10A in its expanded state.

Alternative embodiments of the resilient imaging marker 42 are shown in FIGS. 9A, 9B, 10A and 10B. In FIG. 9A, the embodiment of the resilient imaging marker 142 is a loop of resilient imaging material shown in its compacted state. The loop 142 is shown in its expanded state in FIG. 9B. FIG. 10A shows a second alternate embodiment 242 in its compacted state with the second alternate embodiment 242 shown in its expanded state in FIG. 10B. Other embodiments of the resilient imaging marker 42 are within the scope of the invention. In addition to being detectable by various imaging techniques and resilient, the resilient imaging marker 42 is preferably made out of a material that is not susceptible to bio-degradation when deployed within a living body. Stainless steel is an ideal material from which the resilient imaging marker 42 can be made. "Memory metal" is another suitable material.

Figure 4B:
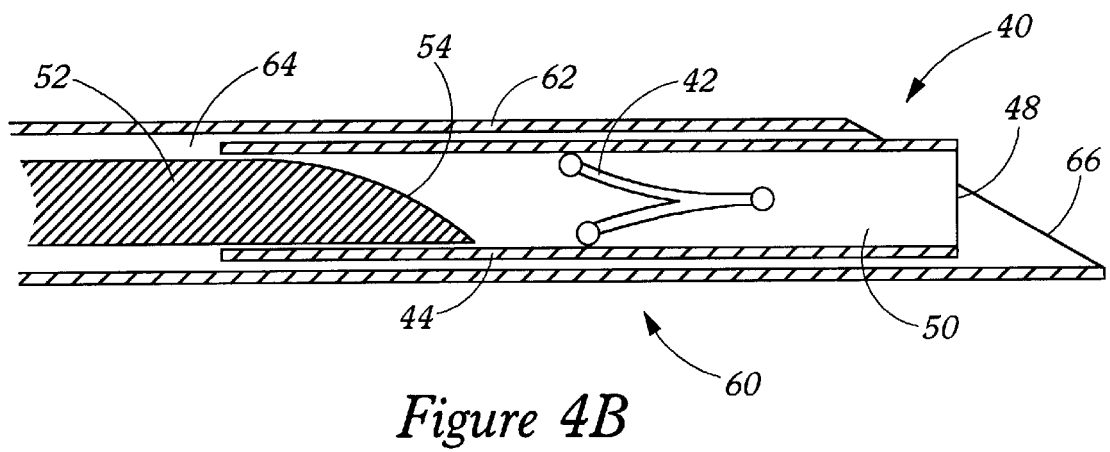
FIG. 4B is the expandable marker in use with a standard aspiration or cutting biopsy needle.

The apparatus for deploying an expandable biopsy marker 40 is shown axially received in a standard aspiration or cutting needle 60 in FIG. 4B. The cutting needle 60 has sidewall 62 defining a needle lumen 64 which extends between an open distal end 66 and a proximal opening, not shown. In use, the aspiration or cutting needle 60 is inserted into tissue or an organ from which a biopsy has been taken and the open distal end 66 is placed at a biopsy void. Thereafter, the deployment catheter 44 provided with the resilient imaging marker 42 residing between the distal opening 48 and the axially inclined surface 54 of the plunger 52 is axially received in a proximal opening (not shown) of the aspiration or cutting needle. The distal opening 48 of the deployment catheter 44 is then advanced to the open distal end 66 of the needle 60. The plunger 52 is then advanced from a deploying position with the resilient imaging marker 42 within the lumen 50 to a deployed position with the resilient imaging marker 42 pushed out of the openings 48 and 66 and into the void. Once the marker is pushed from the openings, it is self-biased from its compacted state as shown in FIG. 4B to its expanded state illustrated in FIG. 7.

Figure 1:
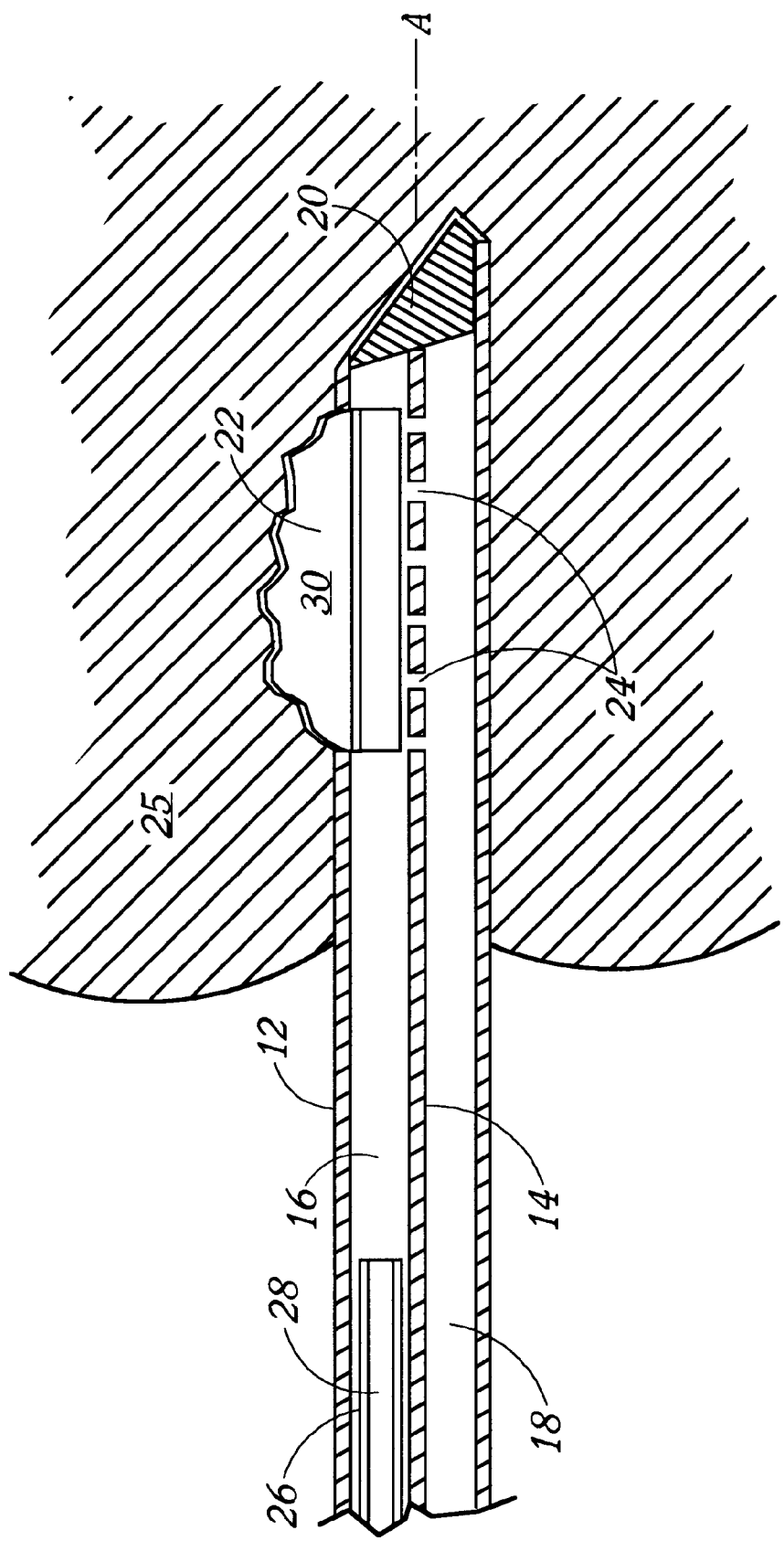
FIG. 1 is an axial cross-section of a dual-lumen biopsy needle with which the apparatus and method for deploying an expandable biopsy marker of the present invention can be used, viewed as a biopsy is being taken.
Figure 2A:
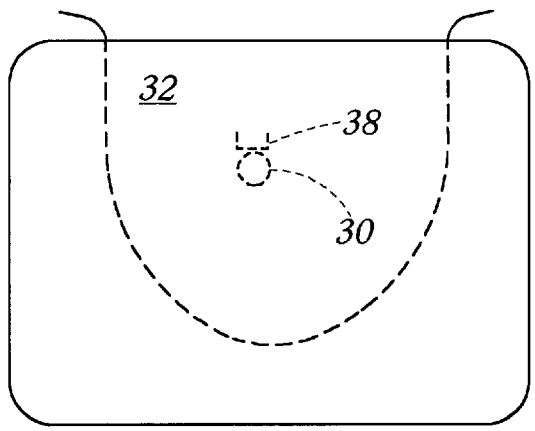
FIG. 2A is a schematic plan view of a breast under compression with a prior art marker being deployed.
Figure 2B:
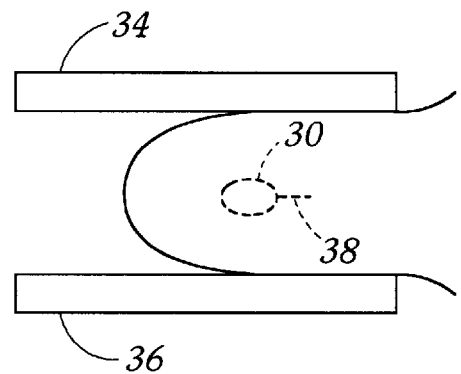
FIG. 2B is a side elevation view of the breast depicted in FIG. 2A.
Figure 3A:
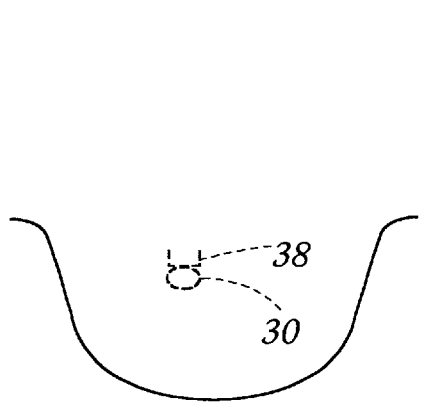
FIG. 3A is a schematic plan view of the breast of FIG. 2A when it is relieved from compression illustrating migration of the marker relative to the biopsy void.
Figure 3B:
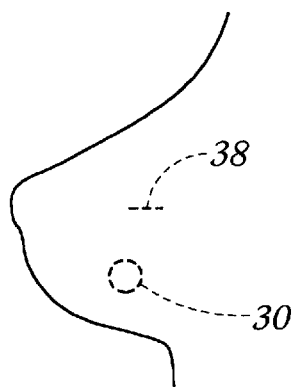
FIG. 3B is a schematic side elevation view of the breast of FIG. 2A when it is relieved from compression illustrating migration of the marker relative to the biopsy void.
Figure 4C:
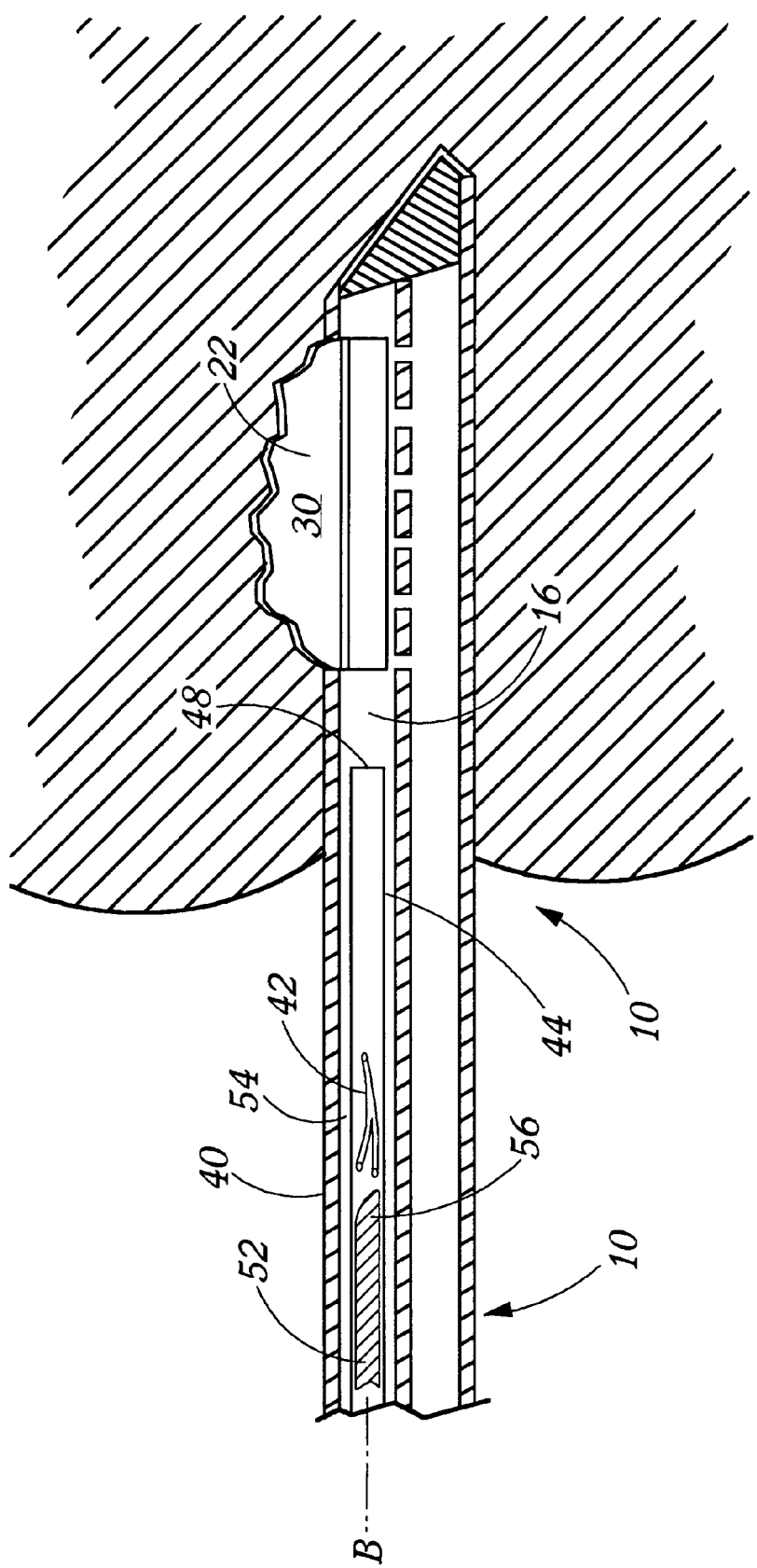
FIG. 4C is an axial cross-section of a dual-lumen biopsy needle of FIG. 1 with a deploying catheter axially advancing the expandable imaging marker in accordance with the present invention.
Figure 5:
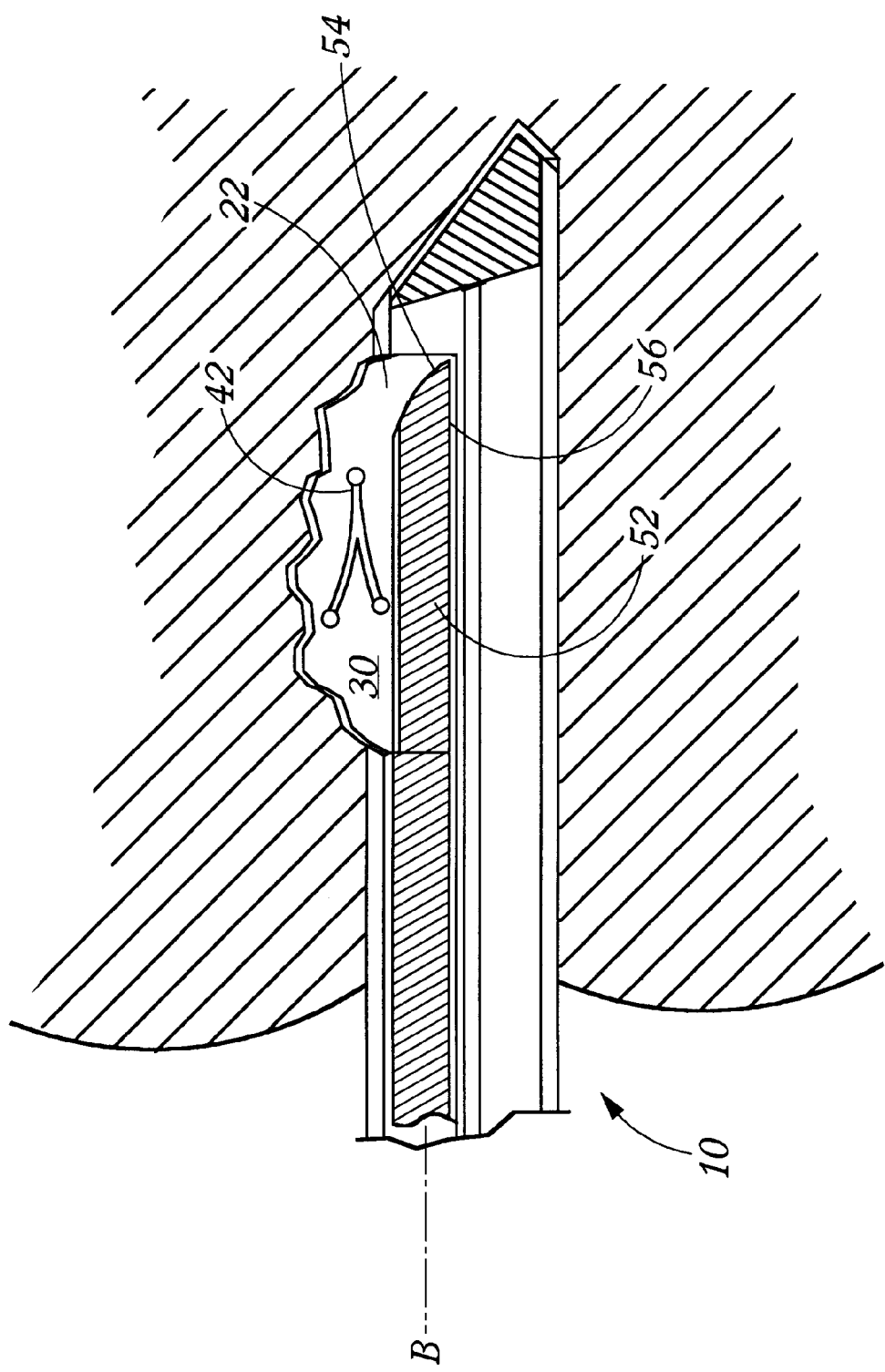
FIG. 5 shows the marker of FIG. 4C in a partially expanded state extending out of the aperture.
Figure 6:
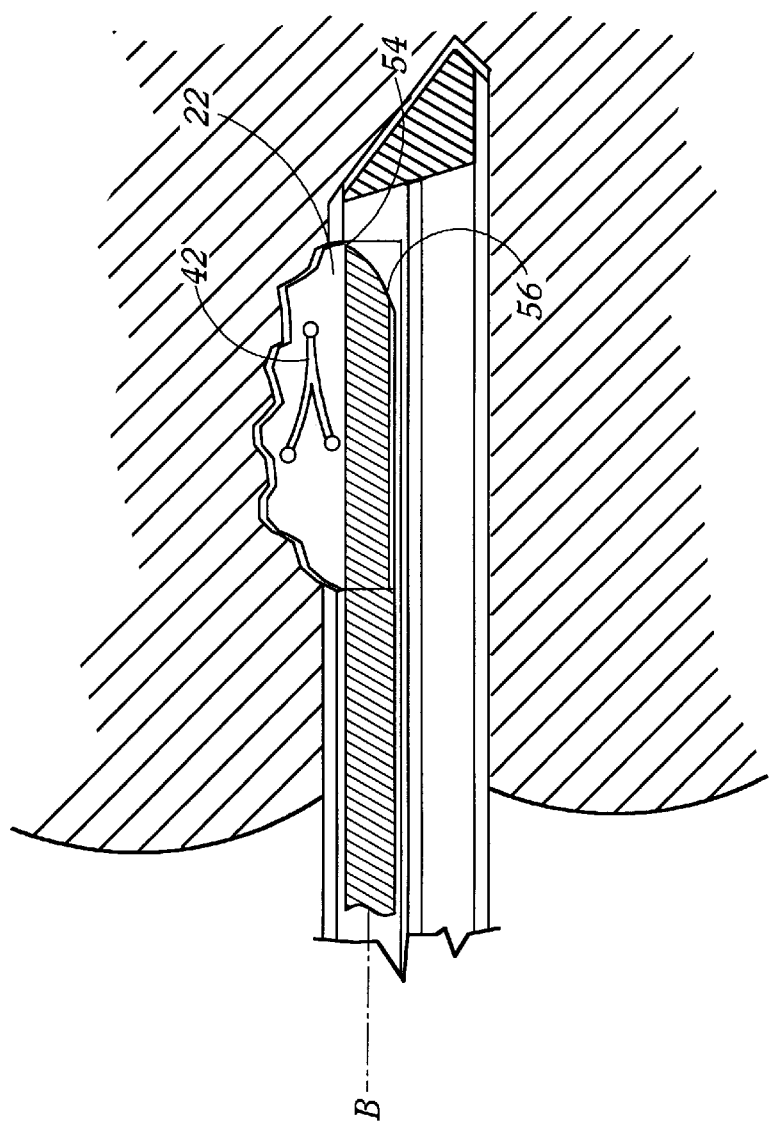
FIG. 6 shows the deploying plunger of FIG. 5 rotated 180 degrees about its axis.

The apparatus for deploying an expandable biopsy marker 40 is shown in FIG. 4C in use with a dual-lumen biopsy needle 10 identical to that described above with regard to FIG. 1 following a biopsy procedure as discussed above with reference to FIG. 1. In this embodiment, the deployment catheter 44 is axially received in the main lumen 16 of the biopsy needle 10. Once the distal opening 48 is moved into proximity with the aperture 22, the plunger 52 is axially advanced from its deploying position to its deployed position which is illustrated in FIG. 5. As it is advanced, the axially inclined surface 54, which is aligned with the aperture 22 in a first orientation, will drive the resilient imaging marker 42 out of the aperture 22. Once the plunger 52 is fully axially advanced as illustrated in FIG. 5, the resilient imaging marker 42 self-biases toward its expanded state out of the aperture 22. The plunger 52 is then rotated 180° about its axis B from the first orientation to a second orientation so that the cylindrical surface 54 is aligned with and substantially closes the aperture 22 as illustrated in FIG. 6. This rotation also urges the marker 42 fully out of the aperture 22. Thereafter, the needle 10 can be withdrawn from the affected tissue without the resilient imaging marker 42 snagging on the mouth of the aperture 22.

Figure 7:
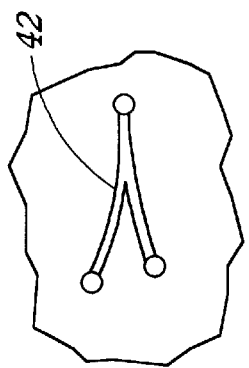
FIG. 7 illustrates the marker of FIG. 4 in a fully expanded state bridging the biopsy void.
Figure 8:
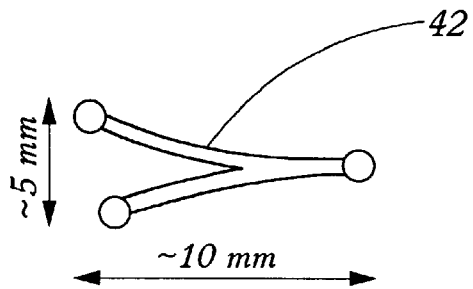
FIG. 8 is a side elevation view of the expandable biopsy maker of FIGS. 4A–C.

Once the needle is removed from the affected tissue, the resilient imaging marker 42 achieves its fully expanded state to substantially bridge the void 30 as illustrated in FIG. 7. Thus, if the marker is deployed in a breast that is under compression, the resilient imaging marker 42 will remain in the void and therefore precisely indicate the location where the biopsy was performed.

While the preferred embodiment of the invention contemplates the use of the deployment catheter 44, the invention also contemplates that the resilient imaging marker 42 could be compressed and inserted directly into an opening at the proximal end of a main lumen 16 of a biopsy needle 10 or the needle lumen 64 of an aspirating or cutting needle 60, with this lumen then preforming the function of the lumen of the deployment catheter. The plunger 52 would then function in the identical manner discussed above. However, use of the deployment catheter is preferred because it could be difficult and time consuming for a physician to compress and insert the imaging marker in this manner.

Figure 11:
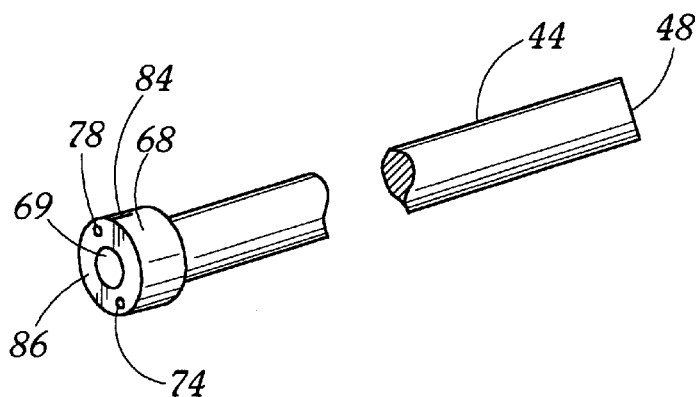
FIG. 11 is a perspective view of a deployment catheter of the present invention.
Figure 12:
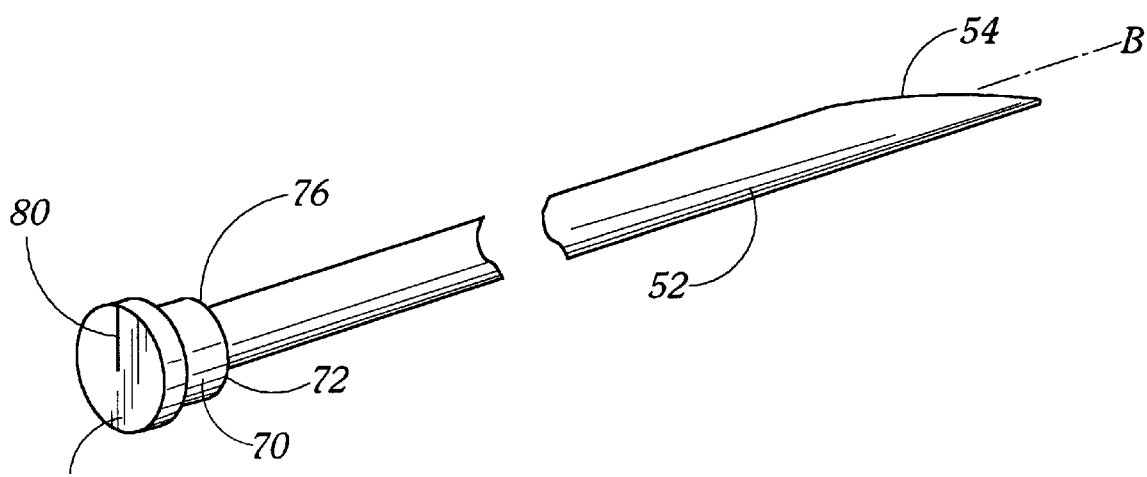
FIG. 12 is a perspective view of a plunger of the present invention.

FIG. 11 shows the deployment catheter having a plastic housing 68 formed at its proximal end about an opening 69. The plunger 52, as illustrated in FIG. 12, may include a knob 70 at its proximal end. Preferably the plunger 52 is of a length such that when the leading end 72 of the knob 70 abuts the trailing end 74 of the housing 68, the axially inclined surface 54 is aligned with the aperture 22 as seen in FIG. 5. In addition, a detent 76 in the leading end 72 of the knob 70 can mate with an indentation 78 in the trailing 74 of the housing 68 to indicate that the axially inclined surface 54 of the plunger 52 is aligned with the aperture 22. Indicia such as the line 80 on the trailing end 82 of the knob 70 corresponds to an indica 84 on the housing 68 to further indicate such alignment. An indentation 86 can also be provided 180 degrees from the indentation 78 in the trailing surface 74 to correspond to the plunger being rotated about its axis B with the cylindrical surface 56 aligned with the aperture 22, as illustrated in FIG. 6. Corresponding indicia (not shown) can be included opposite the indica 84 to indicate closure of the aperture 22. Cooperative structure can also be provided between the leading end 72 of the knob 70 and the trailing end 74 of the housing 68 to provide an audible and/or touch detectable click when the plunger 52 is fully axially advanced to the deployed position within the catheter lumen 50.

The apparatus and method for deploying an expandable biopsy marker of the present invention provides an inexpensive and highly reliable structure for precisely marking the location of a void of tissue left by a biopsy. Precisely marking the biopsy void makes it possible, if further removal of tissue is necessary, for the surgeon to locate the exact site where tissue must be removed so that the tissue can be removed with a minimum of trauma to the patient. In addition, precisely locating the site of the biopsy minimizes the risk that cancerous tissue will be missed when subsequent surgical procedures are required. The apparatus and method for deploying an expandable biopsy marker is compatible with single-lumen and dual-lumen biopsy needles or aspirating needles in common use and can be quickly and easily deployed by a physician. In addition, the simple elegance of the apparatus assures that the marker will in fact be deployed precisely where desired with substantially no risk of either non-deployment or mis-deployment. Furthermore, these many advantages are provided by a structure that is mechanically simple and therefore inexpensive and inherently reliable.

What is claimed is:

1. An apparatus for locating a marker in a void of body tissue created by a biopsy, the apparatus comprising:
   a needle having an axial lumen defined by a side wall of the needle, a proximal opening and an aperture in the side wall extending into the lumen near a distal end of the needle;
   a resilient imaging marker, the imaging marker being adapted to be self-biased to an expanded state in the void of body tissue and compactable to compacted state, the marker in the compacted state residing in the lumen; and
   a plunger having a leading end residing in the axial lumen of the needle, the plunger being axially advancable within the lumen between a deploying position and a deployed position, the leading end positioning the marker at the aperture in the deployed position, whereat the marker self biases to an expanded state extending out of the aperture and into the void of body tissue.

2. The apparatus of claim 1 wherein the leading end of the plunger is configured to drive the marker out of the aperture.

3. The apparatus of claim 1 wherein the leading end of the plunger has an axially inclined surface which, when aligned with the aperture, drives the marker out of the aperture as the plunger is axially advanced to the deployed position.

4. The apparatus of claim 1 wherein the leading end of the plunger has an axially inclined surface and opposite the axially inclined surface a cylindrical surface with an outer diameter substantially corresponding to an inner diameter of the lumen, the cylindrical portion of the leading end, when aligned with the aperture with the plunger in the deployed position, substantially closing the aperture, the marker being driven from the aperture by aligning the inclined surface with the aperture, axially advancing the plunger between the deploying and deployed positions and then axially rotating the plunger to align the cylindrical portion of the leading end with the aperture.

5. The apparatus of claim 1 wherein the resilient imaging marker is made of stainless steel.

6. The apparatus of claim 4 wherein the the plunger has a trailing end opposite the leading end which extends from the proximal opening with the plunger in the deploying position, the apparatus further including indicia associated with the trailing end of the plunger for indicating which of the inclined surface and cylindrical portion of the leading end is aligned with the aperture.

7. The apparatus of claim 1 wherein the imaging marker, in its expanded state, is adapted to substantially bridge the void of body tissue.

8. An apparatus for locating a marker in a void of body tissue created by a biopsy, that apparatus comprising:
   deployment catheter having an axial catheter lumen and an open distal end;
   a resilient imaging marker, the imaging marker being adapted to be self-biased to an expanded state in the void of body tissue and compactable to compacted state, the marker residing in the catheter lumen in its compacted state; and
   a plunger axially received in the lumen of the deployment catheter, the plunger being axially advancable within the catheter lumen between a deploying position and a deployed position, the plunger having a leading end configured to drive the imaging marker out of the open distal end of the deployment catheter and into the void of body tissue upon axial advancement of the plunger from the deploying position to the deployed position, the imaging marker being between the leading end of the plunger and the open distal end of the deployment catheter with the plunger in the deploying position.

9. The apparatus of claim 8 further comprising a needle having an axial needle lumen and proximal and distal ends, the needle further having proximal and distal openings extending into the needle lumen, the distal end of the deployment catheter being axially received in the proximal opening of the needle.

10. The apparatus of claim 9 wherein the distal opening of the needle comprises an open distal end of the needle.

11. The apparatus of claim 8 wherein the leading end of the plunger has an axially inclined surface.

12. The apparatus of claim 9 wherein the distal opening of the needle comprises an aperture in the sidewall of the needle proximate the distal end of the needle and the leading end of the plunger has an axially inclined surface which drives the marker out of the aperture as the leading end of the plunger is axially advanced to the deployed position with the inclined surface aligned with the aperture.

13. The apparatus of claim 12 wherein the leading end of the plunger opposite the axially inclined surface is cylindrical with an outer diameter substantially corresponding to an inner diameter of the catheter lumen, the cylindrical portion of the leading end, when aligned with the aperture with the plunger in the deployed position, substantially closing the aperture, the imaging marker being driven out of the aperture by axially advancing the plunger to the deployed position with the inclined surface aligned with the aperture and then axially rotating the plunger to align the cylindrical portion of the leading end of the plunger with the aperture.

14. The apparatus of claim 13 wherein the plunger includes a trailing end which extends out of a proximal opening of the deployment catheter and the proximal opening of the needle, the trailing end having indicia associated therewith for indicating which of the inclined surface and the cylindrical position of the leading end of the plunger is aligned with the aperture.

15. A method of marking a void of body tissue created by a biopsy, the method comprising:
   a) providing a deployment catheter having an axial lumen and a distal opening with an imaging marker in the axial lumen;
   b) advancing the distal opening of the catheter to a void of body tissue;
   c) axially advancing the imaging marker to the distal opening;
   d) expanding the imaging marker as it reaches the opening to extend into the void of body tissue; and
   e) displacing the imaging marker from the opening so that it resides wholly within the void of body tissue.

16. A method of marking a void of body tissue left by a biopsy performed using a biopsy needle having an axial lumen defined by a side wall of the needle, a proximal opening and an aperture in the side wall extending into the lumen near a distal end of the needle, the aperture being aligned with the void of body tissue, the method comprising:
   a) providing a deployment catheter having an axial lumen and an open distal end with an expandable imaging in the axial lumen;
   b) axially inserting the open distal end of the deployment catheter into the proximal opening of the needle;
   c) axially advancing the imaging marker to the aperture;
   d) expanding the imaging marker as it reaches the aperture to extend into the void of body tissue; and
   e) displacing the imaging marker from the aperture so that it resides wholly within the void of body tissue.

17. The method of claim 16 wherein step e) further comprises:
   closing the aperture.

18. The method of claim 17 further comprising in step d), expanding the imaging marker so that it is adapted to substantially bridge the void of body tissue.

19. The method of claim 17 wherein the expanding of step d) is performed by the imaging marker self-biasing to an expanded state.

20. The method of claim 17 wherein step c) is performed by providing a plunger having a leading end axially received in the open proximal end of the needle and an open proximal end of the deployment catheter, the leading end of the plunger being configured to displace the imaging marker from the aperture by axially rotating the plunger from a first to a second orientation.

21. The method of claim 20 wherein the leading end of the plunger has an axially inclined surface and an opposite cylindrical surface, the axially inclined surface, when aligned with the aperture, urging the marker from the aperture as the plunger is axially advanced from a deploying position with the imaging marker in the lumen to a deployed position with the imaging marker at the aperture and the cylindrical surface, when aligned with the aperture, substantially closing the aperture, the marker being displaced from the aperture in step e) by axially advancing the inclined surface into alignment with the aperture and then axially rotating the plunger to bring the cylindrical surface into alignment with the aperture.

22. A method of marking the site of an internal void of body tissue comprising:
   a) providing an expandable imaging marker;
   b) locating the imaging marker entirely within the internal void; and
   c) expanding the imaging marker within the void.

* * * * *